United States Patent [19]
Claus

[11] Patent Number: 4,851,034
[45] Date of Patent: Jul. 25, 1989

[54] CONTROL OF CERTAIN GRASSES WITH CERTAIN 5-(2-CHLORO-4-(TRIFLUOROMETHYL)-PHENOXY-2-NITROBENZOIC ACID ESTERS AND AMIDES

[75] Inventor: Jon S. Claus, Hanover, Va.

[73] Assignee: Rhone-Poulenc Agrochimie, Lyons, France

[21] Appl. No.: 872,216

[22] Filed: Jun. 9, 1986

Related U.S. Application Data

[63] Continuation of Ser. No. 719,827, Apr. 4, 1985, abandoned, which is a continuation of Ser. No. 473,351, Mar. 8, 1983, abandoned, which is a continuation of Ser. No. 287,406, Jul. 27, 1981, abandoned.

[51] Int. Cl.$^4$ ............................................. C07C 143/77
[52] U.S. Cl. ...................................... 71/107; 564/165; 564/80; 560/65

[58] Field of Search ..................... 71/107; 564/80, 165

[56] References Cited

U.S. PATENT DOCUMENTS

| 3,137,563 | 6/1964 | Newcomer | 71/2.6 |
| 3,282,991 | 11/1966 | Klein et al. | 71/2.6 |
| 3,325,274 | 6/1967 | Anderson | 71/2.6 |
| 4,063,929 | 12/1977 | Bayer | 71/115 |

Primary Examiner—Paul J. Killos
Attorney, Agent, or Firm—Morgan & Finnegan

[57] ABSTRACT

The present invention provides a method for controlling perennial johnsongrass, purple nutsedge, yellow nutsedge and quackgrass with an application of alkyl esters, alkoxycarbonylalkyl esters or alkylsulfonamide salts of 5-[2-chloro-4-(trifluoromethyl)phenoxy]-2-nitrobenzoic acid.

5 Claims, No Drawings

CONTROL OF CERTAIN GRASSES WITH CERTAIN 5-(2-CHLORO-4-(TRIFLUOROMETHYL)-PHENOXY-2-NITROBENZOIC ACID ESTERS AND AMIDES

This is a continuation of co-pending application Ser. No. 719,827 filed Apr. 4, 1985 which is a continuation of application on Ser. No. 473,351 filed Mar. 8, 1983 which is a continuation of Ser. No. 287,406 filed July 27, 1981.

BACKGROUND OF THE INVENTION

Herbicidal 5-[2-chloro-4-(trifluoromethyl)phenoxy]-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chlori forms. U.S. Patents which describe such compounds and the like include U.S. Pat. Nos. 3,652,645; 3,784,635; 3,873,302; 3,983,168; 3,907,866; 3,798,276; 3,928,416; and 4,063,929. The published European Patent Application 3,416 to ICI describes various alkylsulfonamide derivatives of 5-[2-chloro-4-(trifluoromethyl) phenoxy]-2-nitrobenzoic acid including, inter alia, 5-[2-chloro-4-(trifluoromethyl) phenoxy]-2-nitro-N-methanesulfonyl benzamide. The published European Patent Application 20,052 to Rohm and Haas and the published UK Patent Application 2,058,055A to PPG describe various alkoxycarbonylalkyl esters of 5-[2-chloro-4-(trifluoromethyl) phenoxy]-2-nitrobenzoic acid.

According to a particular herbicidal treatment it has been proposed to apply sodium 5-[2-chloro-4-(trifluoromethyl)phenoxy]-2-nitrobenzoate to soybean fields in post-emergence applications to control certain weeds such as broadleaf weeds, e.g., velvetleaf, cocklebur and morningglory. Accordingly, there is a need in the art to provide methods for controlling grass weeds such as johnsongrass.

SUMMARY OF THE INVENTION

The present invention provides a method for controlling grass weed selected from the group consisting of perennial johnsongrass, purple nutsedge, yellow nutsedge and quackgrass in the field under field conditions with an application of a herbicidally effective amount of a compound of the formula

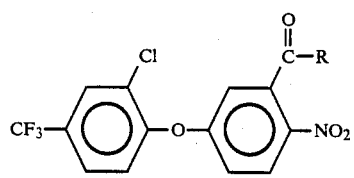

(I)

where R is selected from the group consisting of:
(i) $C_1$–$C_4$ alkoxy (preferably $OCH_3$);
(ii)

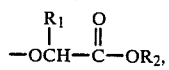

where $R_1$ is H or $C_1$–$C_4$ alkyl and $R_2$ is $C_1$–$C_4$ alkyl;
(iii)

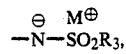

where $R_3$ is $C_1$–$C_4$ alkyl (preferably $CH_3$) and M is alkali metal (preferably Na) or (substituted or unsubstituted) ammonium; and
(IV) $NHSO_2R_3$.

Examples of such (substituted or unsubstituted) ammonium groups may be represented as follows when M is of the formula

where $R_4$, $R_5$, $R_6$ and $R_7$ are the same or different and are selected from the group consisting of H and $C_1$–$C_6$ (substituted or unsubstituted) alkyl.

Particular R groups according to formula I include $OCH_3$, $OCH_2COOC_2H_5$, $OCH(CH_3)COOCH_3$, $OCH_2COOH_3$, $OCH(CH_3)COOC_2H_5$ and $N(Na)SO_2CH_3$.

The compounds of formula (I) which are alkoxycarbonylalkyl esters of 5-[2-chloro-4-(trifluoromethyl)-phenoxy]-2-nitrobenzoic acid may be prepared by techniques known by those of ordinary skill in the art (Note the aforementioned published European Patent Application 20,052 and the published UK Patent Application 2,058,055A).

For example, the compound, ethoxycarbonyl methyl 5-[2-chloro-4-(trifluoromethyl)-phenoxy]-2-nitro-benzoate, has been prepared as follows: To a stirred solution of ethyl glycolate (83.7 g, 0.8 mole) and 5-[2-chloro-4-(trifluoromethyl) phenoxy]-2-nitrobenzoyl chloride (306 g, 0.8 mole) in toluene (800 ml) cooled in an ice bath was added triethylamine (80.8 g, 0.8 mole) dropwise. The exotherm was controlled below 35° C. during addition. The reaction temperature was raised to 62° C. and held for five hours. After cooling the precipitate was filtered. The toluene solution was then washed with 5% sodium hydroxide solution followed by saturated sodium chloride solution. The dried toluene solution was stripped on a rotary evaporator to give 225 g of a brown oil. Vapor phase chromatographic-mass spectral analysis showed that in addition to the desired product there was about 1% of ethyl 5-[2-chloro-4-(trifluoro-methyl)phenoxy]-2-nitrobenzoate and about 9% of ethoxycarbonyl-methoxycarbonylmethyl 5-[2-chloro-4-(trifluoromethyl) phenoxy]-2-nitrobenzoate. The product can be further purified by crystallization from hexane to give an off-white solid.

m.p. 58°–59° C.

I.R. (Neat): C=O, 1745 and 1760 cm$^{-1}$

NMR (CDCl$_3$): triplet 1.30 ppm (3H, J=7.2 Hz); quartet 4.33 ppm (2H, J=7.2 Hz); singlet 4.92 (2H), complex multiplet 7.1–8.1 ppm (5H) and doublet 8.21 ppm (1H, J=9.0 Hz).

A number of compounds of this formula I may alternatively be prepared by displacement of an active halogen (e.g. Haloalkyl X) with the salf of an acid

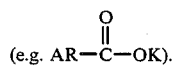

The following is an example of such a procedure.

To a stirred solution of 85% potassium hydroxide (0.66 g, 0.01 mole) in ethanol (25 ml) was added 5-[2-chloro-4-(trifluoromethyl) phenoxy]-2-nitrobenzoic acid. To this mixture was then added ethyl bromoacetate (1.67 g, 0.01 mole) at 30° C. The temperature was raised to 70° C. and maintained for 18 hours. The cooled solution was poured into water and the resulting oil solidified to an off-white solid which was filtered and dried to give 3.85 g (86% yield), m.p. 55°–6° C.

A still further alternative synthesis is shown by the following reaction scheme:

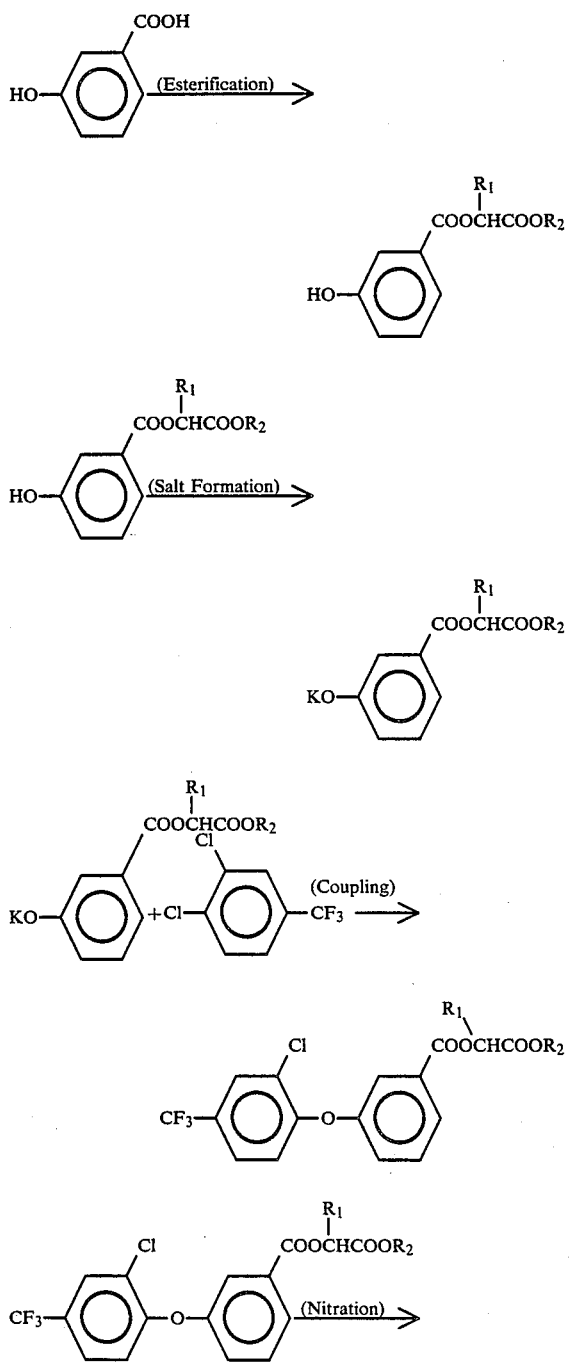

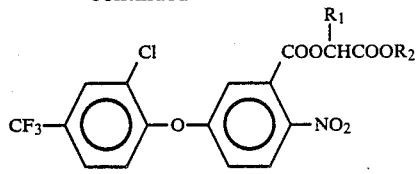

The compounds of formula I, which are alkylsulfonamides, may be formed by the reaction of the corresponding compound of formula I with an appropriate base (e.g., by titration of this free acid with NaOH). This free acid form of the compound of formula I may be formed by any suitable techniques known by those skilled in the act. For example, the procedures discussed in the aforementioned ICI published European Patent Application 3,416 may be followed. However, when $H_2NSO_2CH_3$ is reacted with

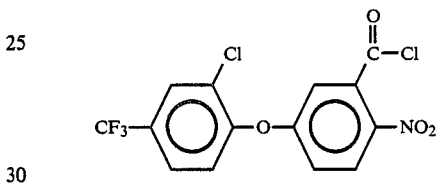

this reaction preferably takes place at elevated temperatures (e.g. at about 150° C.) in the absence of a free acid acceptor such as pyridine.

The compounds of formula I can be applied in various ways to achieve herbicidal action. They can be applied per se, but preferably, may be applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyropyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil. In practice, herbicidal application is measured in terms of pounds of herbicide applied per acre. The compounds of this invention are effective herbicides when applied in herbicidal amounts, e.g., at rates, depending upon climate and soil type, between about 0.03 pound and about 10 pounds per acre. More particularly, the sodium salt of 5-[2-chloro-4-(trifluoromethyl) phenoxy]-2-nitro-N-methanesulfomyl benzomide may preferably be applied at rates of from about ¼ to about 5 lbs./acre, more preferably, from about ½ to about 2 lbs/acre.

The compounds of formula I may be particularly advantageous when used to control perennial johnsongrass, purple nutsedge, yellow nutsedge and quackgrass in fields of crops which are relatively tolerant to these compounds. For instance, soybeans are relatively tolerant to these compounds, particularly depending upon the manner in which these compounds are applied. Accordingly, methyl 5-[2-chloro-4-(trifluoromethyl)-phenoxy]-2-nitrolenzoate is preferably applied to soybean fields to control the above-specified weeds in a pre-plant incorporation application, and alkoxycarbonylalkyl (e.g., ethoxycarbonylmethyl) 5-[2-chloro-4-(trifluoromethyl) pheroxy]-2-nitrobenzoate is preferably applied to soybean fields to control the above-specified weeds in either a pre-plant incorporation application or a pre-emergence application. The salts of 5-[2-chloro-4-(trifluoromethyl) phenoxy]-2-nitro-N-methanesulfonyl benzamide, being highly selective towards soybeans, may be applied to soybean fields to control the above-specified weeds in pre-plant incorporation applications, pre-emergence applications or post-emergence applications. In such pre- and post-emergence applications the salts of 5-[2-chloro-4-(trifluoromethyl) phenoxy]-2-nitro-N-methanesulfonyl benzamide may be applied, e.g., at rates from about ½ to about 2 lb./acre.

EXAMPLE

To a field test plot containing perennial johnsongrass was applied:

(1) methyl 5-[2-chloro-4-(trifluoromethyl)phenoxy]-2-nitrobenzoate at 0.75 lb/acre in a pre-plant incorporation application;

(2) ethoxycarbonylmethyl 5-[2-chloro-4-(trifluoromethyl) phenoxy]-2-nitrobenzoate at 1.5 lb/acre in a pre-plant incorporation application; and (3) ethoxycarbonylmethyl 5-[2-chloro-4-(trifluoromethyl) phenoxy]-2-nitrobenzoate at 0.75 lb/acre in a pre-emergence application.

Perennial johnsongrass was controlled in each of these applications. It is noted that the johnsongrass had sprouted from the rhizome and was 6-8″ tall before evidence of a herbicidal effect was noticed. It is further noted that these tests indicated that the compounds of this example appeared to have a systemic action on johnsongrass.

What is claimed is:

1. A method for controlling at least one grass weed selected from the group consisting of perennial johnsongrass, purple nutsedge, yellow nutsedge and quackgrass in the field under field conditions with an application of a herbicidally effective amount of a compound of the formula:

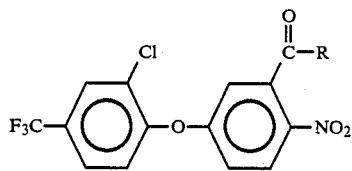

where R is

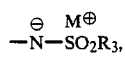

where $R_3$ is $C_1$-$C_4$ alkyl and M is alkali metal or (substituted or unsubstituted) ammonium.

2. A method according to claim 1, wherein said ammonium is of the formula

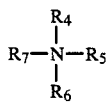

where $R_4$, $R_5$, $R_6$ and $R_7$ are the same or different and are selected from the group consisting of H and $C_1$-$C_6$ (substituted or unsubstituted) alkyl.

3. A method according to claim 1, wherein R is $N(Na)SO_2CH_3$.

4. A method according to claim 1, wherein said compound of formula I is the sodium salt of 5-[2-chloro-4-(trifluoromethyl) phenoxy]-2-nitro-N-methanesulfonyl benzamide and wherein said compound is applied in a post-emergence application to a field containing soybeans.

5. A method according to claim 4, wherein said field comprises perennial johnsongrass in the form of plants or seeds.

* * * * *